United States Patent [19]

Lannert

[11] B 4,013,714

[45] Mar. 22, 1977

[54] SUBSTITUTED BIS-(DICARBOXYMETHYL)-ETHERS

[75] Inventor: Kent P. Lannert, Freeburg, Ill.

[73] Assignee: Monsanto Company, St. Louis, Mo.

[22] Filed: Dec. 19, 1973

[21] Appl. No.: 426,157

[44] Published under the second Trial Voluntary Protest Program on March 23, 1976 as document No. B 426,157.

[52] U.S. Cl. .................. 260/535 P; 252/89 R; 252/132; 252/142; 252/156; 252/546; 252/527; 260/471 R; 260/473 G; 260/484 P; 260/501.1; 260/514 R; 260/343.3 R; 260/343.6; 260/521 R

[51] Int. Cl.$^2$ .................. C07C 59/12

[58] Field of Search .................. 260/535 P

[56] References Cited

UNITED STATES PATENTS 3,293,176  12/1966  While .................. 260/535 P

FOREIGN PATENTS OR APPLICATIONS 2,248,708  4/1973  Germany .................. 260/535 P Primary Examiner—James A. Patten
Assistant Examiner—P. J. Killos Attorney, Agent, or Firm—H. B. Roberts; J. E. Maurer; N. E. Willis

[57] ABSTRACT

Compounds represented by the formula

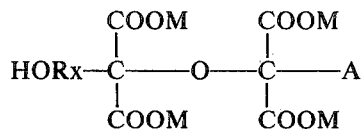

wherein Rx is

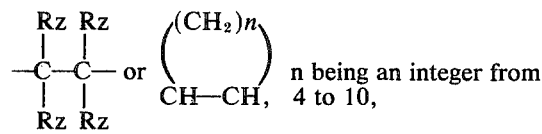

and A is hydrogen, methyl, ethyl, CH$_2$OH or RxOH; M being alkali metal, ammonium, alkyl ammonium, or alkanol ammonium and Rz being hydrogen, alkyl, phenyl, phenyl alkyl, alkoxy alkyl, alkoxy phenyl or alkoxy phenyl alkyl are useful as complexing agents and/or detergency builders. The ester and acid forms of these compounds are useful as intermediates for their preparation.

3 Claims, No Drawings

SUBSTITUTED BIS-(DICARBOXYMETHYL)-ETHERS

BACKGROUND OF THE INVENTION

This invention relates to novel hydroxy ether carboxylate salts useful as complexing agents and detergency builders and to ester and acid forms of such compounds useful as intermediates for preparation of the salts.

The utility of compounds characterized by the ability to complex various metal and alkaline earth metal ions (particularly ions such as calcium ions which contribute to "hardness" of water) in aqueous media and/or provide, in combination with various detergent surfactants, detergent formulations of enhanced cleansing ability is well recognized by those skilled in the art. Such compounds are used in water treating applications (e.g. to "soften" water) and/or as detergency builders.

Although many compounds having complexing and/or detergency builder functionality are known, the provision of novel compounds composed of only carbon, hydrogen and oxygen and having such functionality is desirable.

SUMMARY OF THE INVENTION

It is an object of this invention to provide novel compounds useful as complexing agents and/or detergency builders and intermediates for the synthesis of such compounds.

The compounds of this invention are hydroxy ether polycarboxylic acids, salts and esters whose structure, synthesis, and use will be understood from the following description of the preferred embodiments.

DESCRIPTION OF THE PREFERRED EMBODIMENTS

The compounds of the present invention are represented by the formula

R—O—R' wherein R is

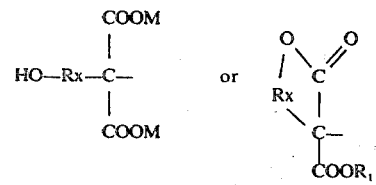

and R' is

when R is

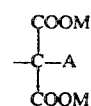

and is

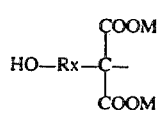

when R is

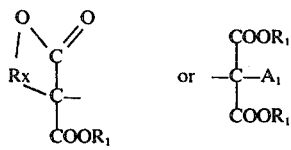

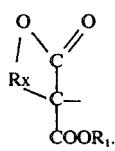

In the above formulae:

M is alkali metal, ammonium, alkyl ammonium containing 1 to 4 carbon atoms or alkanol ammonium containing 1 to 4 carbon atoms;

$R_1$ is hydrogen or an alkyl group containing from 1 to 20 carbon atoms;

A is hydrogen, methyl, ethyl, —$CH_2OH$, or —RxOH;

$A_1$ is hydrogen, methyl, ethyl or —$CH_2OH$;

Rx is

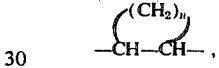

n being an integer from 4 to 10, or

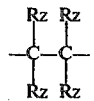

wherein Rz is hydrogen, alkyl, phenyl, phenyl alkyl, alkoxy alkyl, alkoxy phenyl, alkoxy phenyl alkyl or —COOX, X being M when R is

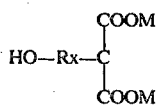

and being $R_1$ when R is

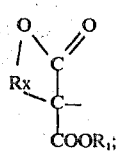

the total number of carbon atoms in Rx being from 2 to 22.

Hereinafter in this application, parenthetical subscripts e, a or s may be used to indicate that the ester, acid or salt forms, respectively, of various moieties are intended. For example, the designation —Rz(e) indicates that if Rz is COOX, X will be an alkyl group.

The above definitions of the moieties constituting the compounds of this invention are intended as individual rather than collective. That is, all Rz substituents need not be identical; a

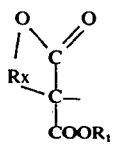

moiety constituting $R_1$ may be different from the

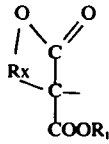

moiety constituting R; etc.

It will be apparent that the compounds in which R is

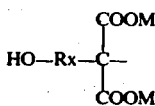

are salt forms of the compounds of this invention whereas the compounds wherein R is

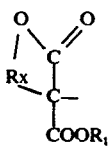

are the acid ($R_1$ and X are hydrogen) or ester ($R_1$ and X are alkyl groups) forms.

The salt forms are useful as complexing agents for metal and alkaline earth metal ions and/or as detergency builders. The ester and acid forms are useful as intermediates for preparation of the salts.

In general, those compounds wherein Rx is

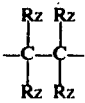

are preferred, the compounds wherein the Rz substituents on the carbon atom adjacent to the hydroxy group or the heterocyclic oxygen are alkyl or, preferably, hydrogen, and the remaining Rz substituents are hydrogen being particularly preferred from the viewpoint of the complexing ability of the salts on a molecular weight basis and the economy of synthesis of the acid and ester forms.

The ester forms of the compounds of this invention (except those in which $A_1$ is $CH_2OH$) are prepared by reacting a compound (whose preparationn will be hereinafter described) represented by the formula

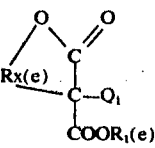

with a compound represented by the formula $Q_2 R_2$.

In the formulae of the above reactants, $Q_1$ is bromine, chlorine or -O-alkali metal; $Q_2$ is bromine or chlorine when $Q_1$ is -O-alkali metal and is -O-alkali metal when $Q_1$ is bromine or chlorine; and $R_2$ is

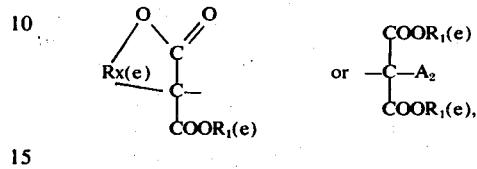

$A_2$ being hydrogen, methyl or ethyl.

This reaction, when $R_2$ is

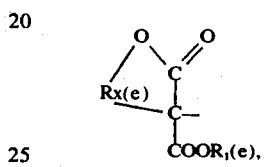

yields the ester form of the invention

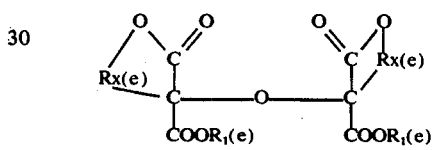

and, when $R_2$ is

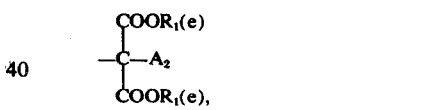

yields the ester form of the invention

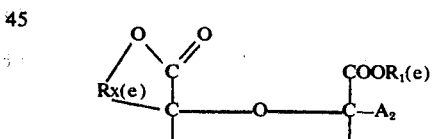

The above reaction is conveniently conducted at temperatures of 0° to 100°C in a solvent for the halogen bearing reactant which is not adversely reactive with the reactants or reaction products (e.g., tetrahydrofuran, ethyl ether, dimethylformamide, etc.).

The ester forms of the compounds of this invention in which $A_1$ is $-CH_2OH$ are prepared by reacting the ester form

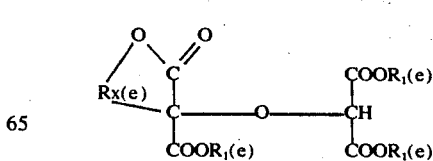

with formaldehyde.

The formaldehyde can be provided directly or materials capable of providing formaldehyde under reaction conditions (e.g., paraformaldehyde, trioxane) can be utilized. Methanol stabilized aqueous formaldehyde solutions (formalin) provide a particularly convenient source of formaldehyde.

The reaction is conducted in a medium sufficiently basic to deprotonate but not so basic as to substantially (more than 30%) hydrolyze or saponify the ester. This degree of basicity is conveniently obtained with a weak base such as potassium bicarbonate. Preferred reaction temperatures are in the range of 15° to 30°C although higher or lower temperatures (generally in the range of 5° to 200°C) can be utilized if desired. At higher temperatures, appropriate pressure or reflux means are desirably employed.

The

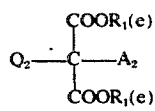

reactants are known and, in general, can be prepared, when $Q_2$ is bromine or chlorine, by reacting bromine or sulfuryl chloride with dialkyl malonate (when $A_3$ is hydrogen) or dialkyl methyl or ethyl malonate (when $A_3$ is methyl or ethyl). The use of the chlorodialkyl malonate and the bromo methyl or ethyl malonate in the reaction is preferred.

The compound wherein $Q_2$ is O-alkali metal is obtained by hydrolysis of the above chloro or bromo malonate, reesterification and treatment of the resultant hydroxy ester with alkali metal or alkali metal hydride.

To prepare the reactant

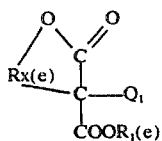

an epoxide of the formula

 (I)

is reacted with a malonic ester of the formula

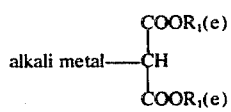 (II)

Epoxides containing the Rx moiety desired for the compound being synthesized can be prepared by known techniques described, for example, in Weissberger, *Heterocyclic Compounds with Three and Four Membered Rings*, Part One, pages 1–523, (interscience Publishers, 1964) and Maliworskii, *Epoxides and Their Derivatives* (Daniel Davey and Co., Inc., 1965) and the various references cited in these publications.

The reaction is conveniently conducted in a mutual solvent for the epoxide (I) and ester (II) which is not adversely reactive with these reactants or the reaction product (the alcohol corresponding to the ester (II) is generally satisfactory) at a temperature of from 0° to 60°C, preferably 40° to 45°C.

The reaction yields

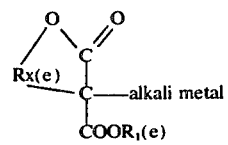 (III)

which is acidified (preferably with acetic acid) to yield

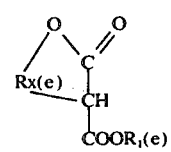 IV

This compound (IV) is bromonated or chlorinated (for example, with elemental bromine or sulfuryl chloride to yield a halolactone (the reactant wherein $Q_1$ is a halogen).

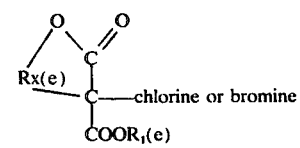 (V)

The bromo compound is generally the preferred halogenated reactant. This halolactone (V) can be converted to the reactant salt

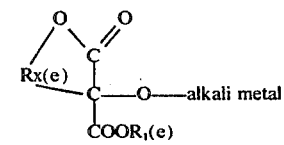 (VI)

by treating the halolactone (V) with alkali metal hydroxide in an alcoholic or aqueous medium to yield

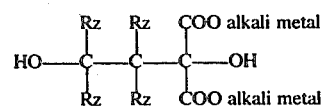

which is re-esterified to the lactone form by conventional procedures and reacted with alkali metal or alkali metal hydride in an inert medium which is a solvent for the ester, e.g., tetrahydrofuran, ether, dimethylformade, etc.

The alkali metal salt forms of the compounds of this invention are prepared either by saponifying the ester forms or neutralizing the acid forms with an alkali metal hydroxide.

The salt can be converted to the acid by treatment with a strong acid, e.g., HCl, $H_2O_4$ or a strong acid ion exchange resin.

The ammonium and alkanol ammonium salt forms of the invention are obtained by treating the acid with ammonia, an alkyl amine, alkanol amine or hydroxides thereof.

The mechanism of epoxide ring opening in the above described processes will favor formation of products wherein the Rz groups attached to the carbon atom adjacent to the heterocyclic oxygen (and, ultimately, the hydroxy group) are of larger spatial configuration than the Rz groups attached to the next carbon atom. However, all possible products will be formed. For example, the epoxide

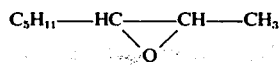

will provide a mixture of lactone reactants of the structures

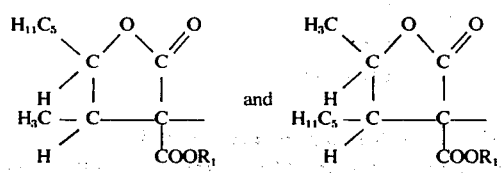

and a mixture of ultimate salt products containing the moieties

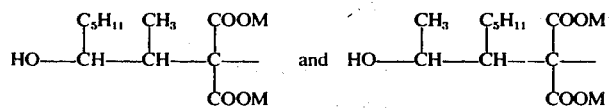

Such mixtures may be utilized as such or separated by conventional techniques.

The hydroxy ether polycarboxylate salts of this invention are useful as agents for complexing metal and/or alkaline earth metal ions in aqueous media. The amount of polycarboxylate required to effectively complex the ions in a given system will depend, to some extent, on the particular polycarboxylate salt being used and the particular metal or alkaline earth metal ions in the aqueous media. Generally, complexing is more effective in basic solution. Optimum conditions and amounts of complexing agent can readily be determined by routine experimentation.

The hydroxy ether polycarboxylate salts are also useful as builders in detergent formulations. Generally, the use of the alkali metal salts, particularly the sodium salt is preferred. However, in some formulations (such as liquid formulations where greater builder solubility is required) the use of ammonium or alkanol ammonium salts may be desirable.

The detergent formulations will contain at least 1% by weight and preferably at least 5% by weight of the hydroxy ether polycarboxylate salts of this invention. In order to obtain the maximum advantages of the builder compositions of this invention, the use of from 5 to 75% of these polycarboxylate salts is particularly preferred. The hydroxy ether polycarboxylate salt compounds of this invention can be the sole detergency builder or these compounds can be utilized in combination with other detergency builders which may constitute from 0 to 95% by weight of the total builders in the formulation. By way of example, builders which can be employed in combination with the novel builder compounds of this invention include water soluble inorganic builder salts such as alkali metal polyphosphates, i.e., the tripolyphosphates and pyrophosphates, alkali metal carbonates, borates, bicarbonates and silicates and water soluble organic builders including amino polycarboxylic acids and salts such as alkali metal nitrilotriacetates, cycloalkane polycarboxylic acids and salts, other ether polycarboxylates, alkyl polycarboxylates, epoxy polycarboxylates, tetrahydrofuran polycarboxylates such as 1,2,3,4 or 2,2,5,5 tetrahydrofuran tetracarboxylates, benzene polycarboxylates, oxidized starches, amino (trimethylene phosphonic acid) and its salts, diphosphonic acids and salts (e.g., methylene diphosphonic acid; 1-hydroxy ethylidene diphosphonic acid) and the like.

The detergent formulations will generally contain from 5 to 95% by weight total builder (although greater or lesser quantities may be employed if desired) which, as indicated above, may be solely the hydroxy ether polycarboxylate salt compounds of this invention or mixtures of such compounds with other builders. The total amount of builder employed will be dependent on the intended use of the detergent formulation, other ingredients of the formulation, pH conditions and the like. For example, general laundry powder formulations will usually contain 20 to 60% builder; liquid dishwashing formulations 11 to 12% builder; machine dishwashing formulations 60 to 90% builder. Optimum levels of builder content as well as optimum mixtures of builders of this invention with other builders for various uses can be determined by routine tests in accordance with conventional detergent formulation practice.

The detergent formulations will generally contain a water soluble detergent surfactant although the surfactant ingredient may be omitted from machine dishwashing formulations. Any water soluble anionic, nonionic, zwitterionic or amphoteric surfactant can be employed.

Examples of suitable anionic surfactants include soaps such as the salts of fatty acids containing about 9 to 20 carbon atoms, e.g., salts of fatty acids derived from coconut oil and tallow; alkyl benzene sulfonates—particularly linear alkyl benzene sulfonates in which the alkyl group contains from 10 to 16 carbon atoms; alcohol sulfates; ethoxylated alcohol sulfates; hydroxy alkyl sulfonates; alkyl sulfates and sulfonates; olefin sulfonates; alkenyl sulfonates; monoglyceride sulfates; acid condensates of fatty acid chlorides with hydroxy alkyl sulfonates and the like.

Examples of suitable nonionic surfactants include alkylene oxide (e.g., ethylene oxide) condensates of mono and polyhydroxy alcohols, alkyl phenols, fatty acid amides, and fatty amines; amine oxides; sugar derivatives such as sucrose monopalmitate; long chain tertiary phosphine oxides; dialkyl sulfoxides; fatty acid amides, (e.g. mono or diethanol amides of fatty acids containing 10 to 18 carbon atoms), and the like.

Examples of suitable zwitterionic surfactants include derivatives of aliphatic quaternary ammonium compounds such as 3-(N,N-dimethyl-N-hexadecylammonio) propane-1-sulfonate and 3-(N,N-dimethyl-N-hexadecylammonio)-2-hydroxy propane-1-sulfonate.

Examples of suitable amphoteric surfactants include betains, sulfobetains and fatty acid imidazole carboxylates and sulfonates.

It will be understood that the above examples of surfactants are by no means comprehensive and that numerous other surfactants are known to those skilled in the art. It will be further understood that the choice and use of surfactants will be in accordance with well understood practices of detergent formulations. For example, anionic surfactants, particularly linear alkyl benzene sulfonate are preferred for use in general laundry formulations, whereas low foaming nonionic surfactants are preferred for use in machine dishwashing formulations.

The quantity of surfactant employed in the detergent formulations will depend on the surfactant chosen and the end use of the formulation. In general, the formulations will contain from 5 to 50% surfactant by weight, although as much as 95% or more surfactant may be employed if desired. For example, general laundry powder formulations normally contain 5 to 50%, preferably 15 to 25% surfactant; machine dishwashing formulations, 0.5 to 5%; liquid dishwashing formulations 20 to 45%. The weight ratio of surfactant to builder will generally be in the range of from 1:12 to 2:1.

In addition to builder and surfactant components, detergent formulations may contain fillers such as sodium sulfate and minor amounts of bleaches, dyes, optical brighteners, soil anti-redeposition agents, perfumes and the like.

In machine dishwashing compositions the surfactant will be a low-foaming nonionic or anionic, preferably nonionic surfactant which will constitute 0 to 5% of the formulation.

The term "low-foaming" surfactant connotes a surfactant which, in the foaming test described below, reduces the revolutions of the washer jet-spray arm during the wash and rinse cycles less than 15%, preferably less than 10%.

In the foaming test, 1.5 grams of surfactant is added to a 1969 Kitchen-Aid Home Dishwasher, Model No. KOS-16, manufactured by Hobart Manufacturing Company which is provided with means for counting revolutions of the washer jet-spray arm during wash and rinse cycles. The machine is operated using distilled water feed at a machine entrance temperature of 40°C. The number of revolutions of the jet-spray arm during the wash and rinse cycles is counted. The results are compared with those obtained by operation of the machine using no surfactant charge, and the percentage decrease in number of revolutions is determined.

The surfactant should, of course, be compatible with the chlorine containing component hereinafter discussed. Examples of suitable nonionic surfactants include ethoxylated alkyl phenols, ethoxylated alcohols (both mono-and di- hydroxy alcohols), polyoxyalkylene glycols, aliphatic polyethers and the like. The widely commercially utilized condensates of polyoxypropylene glycols having molecular weights of from about 1400 to 2200 with ethylene oxide (the ethylene oxide constituting 5 to 35 weight percent of the condensate) are, for example, advantageously used in the machine dishwashing formulations of this invention.

Suitable low-foaming anionic surfactants include alkyldiphenyl ether sulfonates such as sodium dodecyl diphenyl ether disulfonates and alkyl naphthalene sulfonates.

Mixtures of suitable low-foaming surfactants can be utilized if desired.

In addition, machine dishwashing formulations will contain sufficient chlorine providing compound to provide 0.5% to 2% available chlorine. For example, the formulation may contain from 0.5 to 5%, preferably 1 to 3% of a chlorcyanurate or from 10 to 30% chlorinated trisodium phosphate. Suitable chlorocyanurates are sodium and potassium dichlorocyanurate; [(monotrichloro) tetra-(monopotassium dichloro)] pentaisocyanurate; (monotrichloro) (monopotassium dichloro) diisocyanurate.

Machine dishwashing compositions should additionally contain from 5 to 30% soluble sodium silicate having an $SiO_2$ to $Na_2O$ mole ratio of from 1:1 to 3.2:1 preferably about 2.4:1 to inhibit corrosion of metal parts of dishwashing machines and provide over-glaze protection to fine china.

Machine dishwashing compositions will generally contain at least 10%, preferably at least 20% builder, up to a maximum of about 90% builder. The new builder compounds of this invention should constitute at least 5% of the weight of the machine dishwashing formulation in order to obtain the full effects of their inherent characteristics.

The invention is further illustrated by the following examples, wherein all parts and percentages are by weight unless otherwise indicated.

EXAMPLE I

Step 1:
The compound

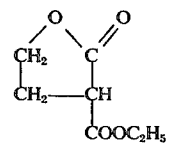 (1)

is prepared by adding 44 grams sodium metal to 900 ml. ethanol and adding 320 grams diethyl malonate to form a slurry of sodium diethyl malonate. To this slurry, 88 grams of ethylene oxide in 300 ml. ethanol is added, the temperature being maintained in the range of 40° to 45°C. The mixture is stirred for 14 hours at a temperature of 25°C and 120 ml. glacial acetic acid is added to form the compound (1). The ethanol is distilled from the slurry under reduced pressure; 500 ml. water is added to the residue to dissolve sodium acetate; the organic product phase is separated, dissolved in ether, washed with water, dried and stripped of ether, and distilled to yield purified

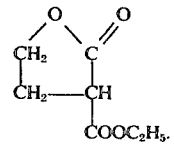 (1)

Step 2:
A solution of 66 grams of this compound (1) in carbon tetrachloride is warmed to about 40°C and bromine is added as the temperature is raised to reflux. Carbon tetrachloride and hydrogen bromide are removed under reduced pressure and residue is diluted with ether and washed with 5% NaHCO₃; saturated NaCl and water; dried and the ether removed leaving

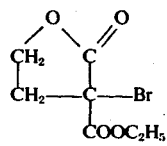 (2)

product.

Step 3:

One hundred twenty-three grams of this product (2) is added to 400 grams of a 25% aqueous potassium hydroxide solution, the temperature being maintained below 45°C. The temperature of the mixture is then held between 40° to 45°C for about 3 hours; raised to and maintained at about 60°C for 12 hours. The mixture is cooled to 10°C, acidified with about 51 ml. concentrated sulfuric acid (a slight excess) and extracted with ether. The extract is washed with saturated sodium chloride solution; dried; filtered; and the ether evaporated. The residue is

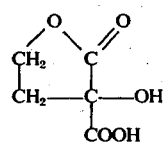 (3)

Step 4:
which is converted to the ester

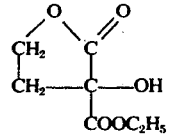 (4)

by conventional esterification procedure.

Step 5:

A solution of 38 grams of this ester (4) in 40 ml. dimethylformamide is added to a slurry of 4.8 grams sodium hydride in 120 ml. dimethylformamide. The mixture is maintained at a temperature of 65° to 70°C until evolution of hydrogen ceases. Diethyl 2-bromo-2-methylmalonate (54.2 grams) is added and mixture temperature is maintained at 67°C for about 3 hours. The mixture is cooled to 25°C; diluted with benzene; washed with water; dried and the benzene removed under vacuum. The residue is vacuum distilled, the product

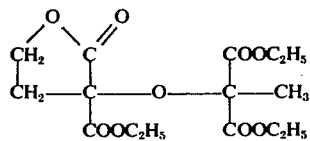 (5)

being collected at 141° to 145°C/0.05 mm. Hg.

Step 6:

Twenty-one grams of this product (5) in 20 ml. ethanol is admixed with 44 grams of 25% aqueous sodium hydroxide solution. After six hours, 100 ml. ethanol is added and the mixture separates into two layers. The upper ethanolic layer is discarded and replaced with fresh ethanol. The lower layer is stirred, the upper layer being repeatedly discarded and replaced with fresh ethanol until the lower layer solidifies. The solid product is

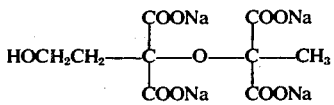 (6)

EXAMPLE II

The compound

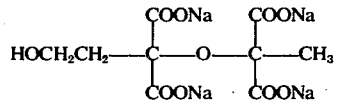

is tested for sequestration function using the procedures described by Matzner et al., "Organic Builder Salts as Replacements for Sodium Tripolyphosphate", Tenside Detergents, 10, Heft 3, pages 119–125 (1973).

The sequestration value (intensity multiplied by capacity expressed as a percentage of sodium tripolyphosphate sequestration value) of

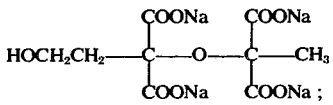

is about 89%. Thus, the compound is seen to be an effective sequestrant.

EXAMPLE III

Detergent formulations containing 50%, 37.5% and 25%

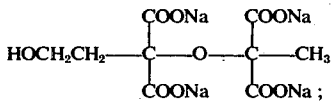

17% linear alkylbenzene sulfonate having an average molecular weight of about 230; 6% sodium silicate and a quantity of sodium sulfate sufficient to equal 100% are found to clean soiled fabrics, in conventional washing operations, substantially more effectively than comparable formulations containing no

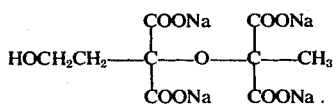

This test shows the compound to be an effective detergency builder.

EXAMPLE IV

Step 5 of Example I is repeated with 41.7 grams of diethyl chloromalonate being substituted for the diethyl 2-bromo-2-methylmalonate to obtain

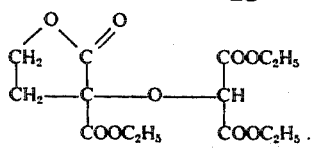 (7)

One mole of this compound (7) is added to a 37% formalin solution (equivalent to 2 moles formaldehyde) containing 0.1 mole potassium bicarbonate and the mixture is stirred for 72 hours. The mixture is extracted with ether and the extract is washed with water, dried and the ether evaporated leaving the product

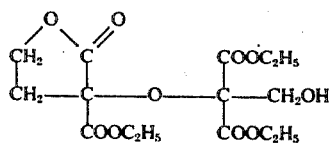 (8)

Treatment of the product (6) pursuant to the procedure of step 6 of Example I yields

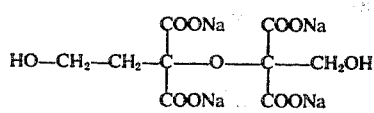 (9)

which, upon testing pursuant to the procedures of Examples II and III is found to be an effective sequestrant and detergency builder.

EXAMPLE V

Step 5 of Example I is repeated with 48 grams of

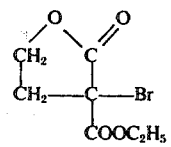

being substituted for the diethyl-2-bromo-2-methylmalonate to obtain the ester

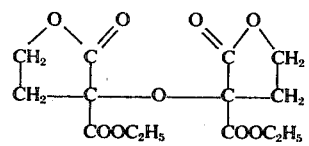 (10)

Treatment of the ester (10) pursuant to the procedure of step 6 of Example I yields

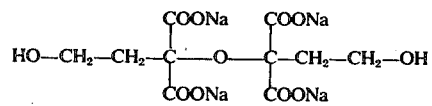 (11)

which, upon testing pursuant to the procedures of Examples II and III is found to be an effective sequestrant and detergency builder.

Table I below exemplifies other products of the invention which can be obtained by reaction of the reactants shown in the first two columns followed by saponification with sodium hydroxide pursuant to the processes described herein.

TABLE I

| REACTANTS | | SAPONIFIED PRODUCT |
|---|---|---|
| ![structure with H3C, H, H2C, ONa, COOC2H5 on 5-membered ring] | BrC(CH3)(COOC2H5)2 | HO—CH(CH3)—C(CH3)(COONa)—O—C(CH3)(COONa)—CH3 |
| and | | and |
| ![structure with H2C, H, CH3, ONa, COOC2H5] | | HO—CH2—CH(CH3)—C(COONa)(CH3)—O—C(CH3)(COONa)—CH3 |
| (derived from H2C—O—CH—CH3) | | |
| ![structure with H3C, H, H3C, H, ONa, COOC2H5] | BrC(CH3)(COOC2H5)2 | HO—CH(CH3)—CH(CH3)—C(CH3)(COONa)—O—C(CH3)(COONa)—CH3 |
| (derived from CH3—C(H)—O—C(H)—CH3) | | |

TABLE I-continued
| REACTANTS | | SAPONIFIED PRODUCT |
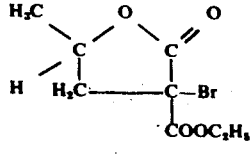

TABLE I-continued

| REACTANTS | SAPONIFIED PRODUCT |
|---|---|
| (derived from 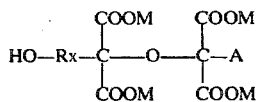 ) | |
| [structure with CH₂ groups, lactone, —ONa, —COOC₂H₅]    Br—C(COOC₂H₅)(CH₃)(COOC₂H₅) | HO—CH(CH₂—CH₂—CH₂—CH₂)—CH—C(COONa)(COONa)—O—C(COONa)(COONa)—CH₃ |
| (derived from  ) | |

What is claimed is:

1. A compound represented by the formula $$HO-Rx-\underset{\underset{COOM}{|}}{\overset{\overset{COOM}{|}}{C}}-O-\underset{\underset{COOM}{|}}{\overset{\overset{COOM}{|}}{C}}-A$$

wherein M is selected from the group consisting of alkali metal, ammonium, alkyl ammonium containing 1 to 4 carbon atoms and alkanol ammonium containing 1 to 4 carbon atoms; A is selected from the group consisting of hydrogen, methyl, ethyl, —CH₂OH and RxOH; and Rx is $$-\underset{\underset{Rz}{|}}{\overset{\overset{Rz}{|}}{C}}-\underset{\underset{Rz}{|}}{\overset{\overset{Rz}{|}}{C}}-,$$

Rz being selected from the group consisting of hydrogen, alkyl, alkoxy alkyl, and —COOM, the total number of carbon atoms in Rx being from 2 to 22.

2. A compound according to claim 1 wherein all Rz substituents are hydrogen.

3. A compound according to claim 2 wherein —A is —CH₃ and M is sodium.

* * * * *